US007232903B2

United States Patent
Nishino et al.

(10) Patent No.: US 7,232,903 B2
(45) Date of Patent: Jun. 19, 2007

(54) PROCESS FOR PRODUCING QUINAZOLIN-4-ONE AND DERIVATIVES THEREOF

(75) Inventors: Shigeyoshi Nishino, Yamaguchi (JP); Kenji Hirotsu, Yamaguchi (JP); Hidetaka Shima, Yamaguchi (JP); Takashi Harada, Yamaguchi (JP); Hiroyuki Oda, Yamaguchi (JP)

(73) Assignee: Ube Industries, Ltd. (JP)

( * ) Notice: Subject to any disclaimer, the term of this patent is extended or adjusted under 35 U.S.C. 154(b) by 0 days.

(21) Appl. No.: 10/499,361

(22) PCT Filed: Dec. 19, 2002

(86) PCT No.: PCT/JP02/13321

§ 371 (c)(1),
(2), (4) Date: Jun. 18, 2004

(87) PCT Pub. No.: WO03/051849

PCT Pub. Date: Jun. 26, 2003

(65) Prior Publication Data

US 2005/0124809 A1    Jun. 9, 2005

(30) Foreign Application Priority Data

Dec. 19, 2001  (JP)  .............................. 2001-385593
Jan. 16, 2002  (JP)  .............................. 2002-007014

(51) Int. Cl.
    *C07D 239/88*    (2006.01)
(52) U.S. Cl. .................................................. 544/287
(58) Field of Classification Search ............... 544/287, 544/255, 283; 562/456
    See application file for complete search history.

(56) References Cited

U.S. PATENT DOCUMENTS 4,644,065 A * 2/1987 Vinogradoff ................. 548/254
5,710,158 A * 1/1998 Myers et al. ............. 514/266.2
5,962,458 A * 10/1999 Lohmann et al. ...... 514/266.21

FOREIGN PATENT DOCUMENTS

| EP | 1 029 853 A1 | | 8/2000 |
|---|---|---|---|
| GB | 1199768 | * | 7/1970 |
| JP | 61-52277 | | 3/1986 |
| JP | 9-508126 | | 8/1997 |
| WO | WO 95/19970 | | 7/1995 |
| WO | WO 02/36587 A2 | | 5/2002 |

OTHER PUBLICATIONS

March, J. Advanced Organic Chemistry—Reactions, Mechanisms, and Structure. 4th Edition, (c) 1992, John Wiley & Son, Inc., New York, NY, p. 419, Section 0-54.*
Kirk et al., Formic Acid-Encyclopedia of Reagents for Organic Synthesis, John Wiley & Sons Ltd, pp. 1-6, 2001.*
Taylor et al., Triethyl Orthoformate-Encyclopedia of Reagents for Organic Synthesis, John Wiley & Sons Ltd, pp. 1-7, 2001.*
Jan Bergman et al., "Syntheses of Gem-Dinitro Heterocyclic Compounds, their Ring-Opening Reactions and Transformations Into Indoles, Indazoles, and Benzoxazinones", Tetrahedron (1999), 10447-10466, 55(34).
W. Brzyska et al., "Preparation , properties and thermal decomposition of Y(III) and lanthanide (III) complexes with 2-amino-5-chlorobenzoic acid", Polish Journal Of Chemistry (1997), 1518-1524, 71(11).
R. Mrozek et al. "Thermal decomposition of rare earth complexes with 2-amino-3, 5-dichlorobenzoic acid", Synthesis and Reactivity in Inorganic and Metal-Organic Chemistry (1997), 707-720, 27(5).
Freer and Sherman, "*Formamide And Its Sodium And Silver Salts*", American Chemical Journal, 20, Contribution from the Laboratory of General Chemistry, University of Michigan, pp. 223-228 (1898).
V.P. Shamshin, et al., "*Search For New Drugs*- Synthesis and Neurotropic Activity of (Heterylphenylmethyl)-Amines and-Ureas," Pharmaceutical Chemistry Journal, vol. 35. No. 7, (2001)(Translated from Khimiko-Fannatsevticheskii Zhurnal, vol. 35, No. 7. pp. 3-6, Jul. 2001).
Supplemental Partial European Search Report/EP 02 80 5031/ mailed Mar. 29, 2006.
Baker B.R. et al., *Journal of Organic Chemistry*, "An Antimalarial Alkaloid from Hydrangea. XIX: Thiophene Isosters", vol. 18, No. 2, pp. 138-152 (1953).
Segar, C. et al., *Chemical and Pharmaceutical Bulletin*, "Structure Elucidation and Synthesis of a New Bioactive Quinazolone Derivative Obtained from Glycosmis Cf. Chlorosperma", vol. 46, No. 12, pp. 1926-1928 (1998).
Beilstein GmbH and MDL Information Systems GmbH; XP002374573, see Reaction ID=623483 & Atti Accad. Naz. Lincei C1. Sci. Fis. Mat. Nat. Rend., vol. 6, nr. 28, pp. 96-98 (1938).

* cited by examiner

*Primary Examiner*—Venkataraman Balasubramanian
(74) *Attorney, Agent, or Firm*—Nixon Peabody LLP; Jeffrey L. Costellia

(57) ABSTRACT

A process for preparing quinazolin-4-one or its derivative by reacting anthranilic acid or its derivative with formic acid or its derivative in the presence of ammonia, or by reacting ammonium anthranilate or its derivative with formic acid or its derivative.

4 Claims, No Drawings

PROCESS FOR PRODUCING QUINAZOLIN-4-ONE AND DERIVATIVES THEREOF

FIELD OF THE INVENTION

The present invention relates to a process for preparing quinazolin-4-one or its derivatives from anthranilic acid or its derivatives or ammonium anthranilate or its derivatives. The quinazolin-4-one and its derivatives are useful as intermediates or starting compounds for preparing pharmaceutically active compounds or agricultural chemicals.

BACKGROUND OF THE INVENTION

The following processes are known for preparing quinazolin-4-one or its derivatives from anthranilic acid or its derivatives.

1) EP 1029853 discloses a process for preparing 6-iodoquinazolin-4-one by reacting 5-iodoanthranilic acid with formamidine acetate in ethanol for 20 hours. This process has problems in that the reaction period is long, and it is necessary to use expensive formamidine in an excessive amount.

2) Chem. Pharm. Bull., 46, 1926 (1998) describes a process for preparing quinazolin-4-one by reacting anthranilic acid with formamide. This process has a problem in that teratogenetic formamide is used in an excessive amount.

Thus, these processes have various problems, and hence are not satisfactory as industrially employable processes for preparing quinazolin-4-one or its derivatives.

SUMMARY OF THE INVENTION

The present invention has an object to provide an industrially advantageous simple process for preparing quinazolin-4-one or its derivatives from anthranilic acid or its derivatives or ammonium anthranilate or its derivatives in high yields under moderate conditions.

The present invention resides in a process for preparing quinazolin-4-one or a derivative thereof having the formula (2):

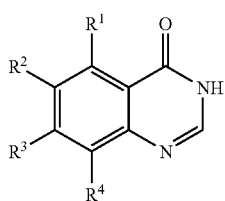

in which each of $R^1$, $R^2$, $R^3$ and $R^4$ independently represents a hydrogen atom, a halogen atom, or a group that does not participate in the following reaction and may have a substituent, or $R^1$, $R^2$, $R^3$ and $R^4$ may be combined to form a ring, which is characterized in that an anthranilic acid or a derivative thereof having the formula (1):

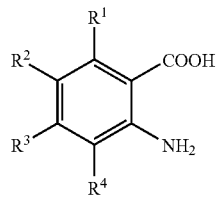

in which each of $R^1$, $R^2$, $R^3$ and $R^4$ has the same meaning as above, is reacted with formic acid or a derivative thereof in the presence of ammonia.

The invention further relates to a process for preparing quinazolin-4-one or a derivative thereof having the above-mentioned formula (2) which is characterized in that ammonium anthranilate or a derivative thereof having the formula (3):

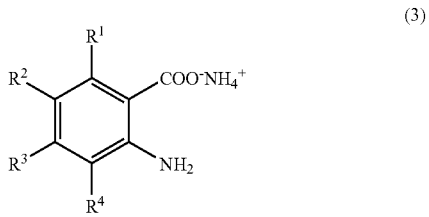

in which each of $R^1$, $R^2$, $R^3$ and $R^4$ independently represents a hydrogen atom, a halogen atom, or a group that does not participate in the following reaction and may have a substituent, or $R^1$, $R^2$, $R^3$ and $R^4$ may be combined to form a ring, is reacted with formic acid or a derivative thereof.

DETAILED DESCRIPTION OF THE INVENTION

The anthranilic acid or a derivative thereof employed in the invention is represented by the above-mentioned formula (1). In the formula (1), each of $R^1$, $R^2$, $R^3$ and $R^4$ is the same or different and is a hydrogen atom, a halogen atom, or a group that does not participate in the reaction and may have a substituent. In more detail, each is hydrogen, alkyl, cycloalkyl, aralkyl, aryl, halogen, hydroxyl, alkoxy, alkylthio, nitro, cyano, carbonyl, or amino (not for $R^1$). Otherwise, $R^1$, $R^2$, $R^3$ and $R^4$ may be combined to form a ring. The alkyl contained in these groups preferably has 1 to 12 carbon atoms.

Examples of the alkyl groups include methyl, ethyl, propyl, butyl, pentyl, hexyl, heptyl, octyl, nonyl, and decyl. These groups can be any of isomers. Examples of the cycloalkyl groups include cyclopropyl, cyclobutyl, cyclopentyl, cyclohexyl, cycloheptyl, and cyclooctyl. Examples of the aralkyl groups include benzyl, phenethyl, and phenylpropyl. These groups can be any of isomers. Examples of the aryl groups include phenyl, p-tolyl, naphthyl, and anthranyl. These groups can be any of isomers. Examples of halogen atoms include fluorine, chlorine, bromine, and iodine. Examples of the alkoxy groups include methoxy, ethoxy, and propoxy. These groups can be any of isomers. Examples of the alkylthio groups include methylthio, ethylthio, and propylthio. These groups can be any of isomers.

The above-mentioned alkyl, cycloalkyl, aralkyl, aryl, alkoxy, alkylthio, and amino(not for $R^1$) may have a substituent. Examples of the substituents include a substituent bonded via a carbon atom, a substituent bonded via an oxygen atom, a substituent bonded via a nitrogen atom, a substituent bonded via a sulfur atom, and a halogen atom.

Examples of the substituents bonded via a carbon atom include alkyl groups such as methyl, ethyl, propyl, butyl, pentyl, and hexyl; cycloalkyl groups such as cyclopropyl, cyclobutyl, cyclopentyl, and cyclohexyl; alkenyl groups such as vinyl, allyl, propenyl, cyclopropenyl, cyclobutenyl, and cyclopentenyl; heterocyclic alkenyl groups such as pyrrolidinyl, pyrrolyl, furyl, and thienyl; aryl groups such as phenyl, tolyl, xylyl, biphenylyl, naphthyl, anthryl, and phenanthoryl; acyl groups (may be acetallized) such as formyl, acetyl, propionyl, acryloyl, pivaloyl, cyclohexylcarbonyl, benzoyl, naphthoyl, and toluoyl; carboxyl groups; alkoxycarbonyl groups such as methoxycarbonyl and ethoxycarbonyl; aryloxycarbonyl groups such as phenoxycarbonyl; halogenated alkyl groups such as trifluoromethyl; and cyano group. These groups can be any of isomers.

Examples of the substituents bonded via an oxygen atom include hydroxyl; alkoxy groups such as methoxy, ethoxy, propoxy, butoxy, pentyloxy, hexyloxy, heptyloxy, and benzyloxy; and aryloxy groups such as phenoxy, toluyloxy, and naphthyloxy. These groups can be any of isomers.

Examples of the substituents bonded via a nitrogen atom include primary amino groups such as methylamino, ethylamino, butylamino, cyclohexylamino, phenylamino, and naphthylamino; secondary amino groups such as dimethylamino, diethylamino, dibutylamino, methylethylamino, methylbutylamino, and diphenylamino; heterocyclic amino groups such as morpholino, piperidino, piperazinyl, pyrazolidinyl, pyrrolidino, and indolyl; and imino group. These groups can be any of isomers.

Examples of the substituents bonded via a sulfur atom include mercapto; thioalkoxy groups such as thiomethoxy, thioethoxy, and thiopropoxy; and thioaryloxy groups such as thiophenoxy, thiotoluyloxy, and thionaphthyloxy. These groups can be any of isomers.

Examples of the halogen atoms include fluorine, chlorine, bromine, and iodine.

The ammonium anthranilate and its derivatives employable in the invention are represented by the aforementioned formula (3). $R^1$, $R^2$, $R^3$ and $R^4$ seen in the formula (3) have the same meanings as described hereinbefore.

Examples of the formic acid and its derivatives include formic acid; formic acid esters such as methyl formate and ethyl formate; and orthoformic acid esters such as methyl orthoformate and ethyl orthoformate. Preferred are formic acid esters and orthoformic acid esters. More preferred are orthoformic acid esters. Specifically preferred are methyl orthoformate and ethyl orthoformate.

The formic acid or its derivatives can be preferably employed in an amount of 1.0 to 10 moles, more preferably 1.1 to 3.0 moles, per one mole of anthranilic acid or its derivatives or ammonium anthranilate or its derivatives.

The ammonia employed in the reaction can be liquid ammonia or gaseous ammonia. Preferred is a solution of ammonia in an organic solvent such as alcohol (e.g., methanol) and ether (e.g., dioxane). In the latter case, the ammonia solution is of a concentration of, preferably, 1 to 90 wt. %, more preferably 3 to 30 wt. %. The ammonia is preferably employed in an amount of 1 to 60 moles, more preferably 2 to 20 moles, per one mole of anthranilic acid or its derivative.

The reaction of the invention can be conducted in the presence or absence of a solvent. There are no limitation with respect to the solvents employed in the reaction, provided that the solvents do not disturb the reaction. Examples are alcohols such as methanol, ethanol, isopropyl alcohol, n-butyl alcohol, and t-butyl alcohol; amides such as N,N-dimethylformamide and N-methylpyrrolidone; ureas such as N,N'-dimethylimidazolidinone; sulfoxides such as dimethyl sulfoxide; aromatic hydrocarbons such as benzene, toluene, xylene, and mesitylene; halogenated aliphatic hydrocarbons such as methylene chloride, chloroform, and dichloroethane; nitrites such as acetonitrile and propionitrile; and ethers such as diethyl ether, tetrahydrofuran, and dioxane. Preferred are alcohols. More preferred are methanol and ethanol. These solvents can be employed singly or in combination.

The amount of the solvent employed in the reaction depends on the homogeneity and stirring condition of the reaction mixture. It is preferred that the solvent is employed in an amount of 0 to 50 g (more preferably 0 to 20 g, most preferably 0 to 5 g) per one gram of the anthranilic acid or its derivative or ammonium anthranilate or its derivative.

The reaction of the invention can be performed, for instance, by mixing and stirring the compounds to be involved in the invention. The reaction is preferably performed at a temperature of 40 to 200° C., more preferably 50 to 150° C. There is no limitation with respect to the pressure for the reaction.

After the reaction is complete, the final product, i.e., quinazolin-4-one or its derivative, can be isolated and purified by the conventional procedures such as concentration, distillation, recrystallization, and column chromatography.

The invention is further described by the following examples.

EXAMPLE 1

Preparation of quinazolin-4-one

In a 2-mL volume stainless steel pressure-resistant vessel were placed 260 mg (1.9 mmol) of anthranilic acid, 403 mg (3.8 mmol) of methyl orthoformate, and 1.2 mL (8.4 mmol) of 15 wt. % ammonia methanol solution. The reaction was carried out at 120° C. for 2 hours. After the reaction was complete, the reaction mixture was cooled to room temperature and analyzed (according to absolute quantitative analysis) by high performance liquid chromatography. There was produced 278 mg (reaction yield: 100%) of quinazolin-4-one.

EXAMPLE 2

Preparation of 7-chloroquinazolin-4-one

In a 2-mL volume stainless steel pressure-resistant vessel were placed 330 mg (1.9 mmol) of 4-chloroanthranilic acid, 403 mg (3.8 mmol) of methyl orthoformate, and 1.2 mL (8.4 mmol) of 15 wt. % ammonia methanol solution. The reaction was carried out at 120° C. for 2 hours. After the reaction was complete, the reaction mixture was cooled to room temperature and analyzed (according to absolute quantitative analysis) by high performance liquid chromatography. There was produced 343 mg (reaction yield: 99%) of 7-chloroquinazolin-4-one.

EXAMPLE 3

Preparation of 6-iodoquinazolin-4-one

In a 2-mL volume stainless steel pressure-resistant vessel were placed 500 mg (1.9 mmol) of 5-iodoanthranilic acid, 403 mg (3.8 mmol) of methyl orthoformate, and 1.2 mL (8.4 mmol) of 15 wt. % ammonia methanol solution. The reaction was carried out at 120° C. for 2 hours. After the reaction was complete, the reaction mixture was cooled to room temperature and analyzed (according to absolute quantitative analysis) by high performance liquid chromatography. There was produced 515 mg (reaction yield: 99%) of 6-iodoquinazolin-4-one.

EXAMPLE 4

Preparation of 6-iodoquinazolin-4-one

The procedures of Example 3 were repeated except that the reaction temperature and reaction period were changed to 95° C. and 4 hours, respectively. There was produced 485 mg (reaction yield: 93%) of 6-iodoquinazolin-4-one.

EXAMPLE 5

Preparation of 6-iodoquinazolin-4-one

The procedures of Example 3 were repeated except that the amount of methyl orthoformate was changed to 320 mg (3.0 mmol). There was produced 514 mg (reaction yield: 99%) of 6-iodoquinazolin-4-one.

EXAMPLE 6

Preparation of 6-iodoquinazolin-4-one

In a 200 mL volume stainless steel pressure-resistant vessel equipped with a thermometer, an pressure gauge, and a stirrer were placed 25.0 g (95 mmol) of 5-iodoanthranilic acid, 17.1 g (162 mmol) of methyl orthoformate, and 50 mL (349 mmol) of 15 wt. % ammonia methanol solution. The reaction was carried out at a temperature of 100-110° C. and a pressure of 0.5 MPa (gauge pressure) for 8 hours. After the reaction was complete, the reaction mixture was cooled to a temperature of 0-10° C. and placed under reduced pressure to distill ammonia off. The residual reaction mixture was then stirred at 0° C. for one hour. The precipitated solid was collected by filtration and dried, to obtain 24.3 g (isolated yield: 94%) of 6-iodoquinazolin-4-one as a pale gray crystalline product.

EXAMPLE 7

Preparation of 6-iodoquinazolin-4-one

In a 2-mL volume stainless steel pressure-resistant vessel were placed 500 mg (1.9 mmol) of 5-iodoanthranilic acid, 342 mg (5.7 mmol) of methyl formate, and 1.2 mL (8.4 mmol) of 15 wt. % ammonia methanol solution. The reaction was carried out at 150° C. for 4 hours. After the reaction was complete, the reaction mixture was cooled to room temperature and analyzed (according to absolute quantitative analysis) by high performance liquid chromatography. There was produced 401 mg (reaction yield: 77%) of 6-iodoquinazolin-4-one.

EXAMPLE 8

Preparation of 6-iodoquinazolin-4-one

The procedures of Example 7 were repeated except that methyl formate was changed to 263 mg (5.7 mmol) of formic acid. There was produced 302 mg (reaction yield: 58%) of 6-iodoquinazolin-4-one.

Reference Example 1

Preparation of Ammonium Anthranilate

In a 50 mL volume glass vessel equipped with a stirrer and a thermometer were placed 5.0 g (36.5 mmol) of anthranilic acid and 20 mL (156 mmol) of 15 wt. % ammonia methanol solution. The reaction was carried out for 2 hours at room temperature. After the reaction was complete, the reaction mixture was concentrated under reduced pressure, to obtain 5.0 g (isolated yield: 94%) of ammonium anthranilate as white solid.

The physical characteristics of the ammonium anthranilate were described below.

m.p. (sublimation): 145 to 146° C.

$^1$H-NMR (DMSO-$d_6$, δ (ppm)): 6.37-6.43 (1 H, m), 6.56 (1 H, dd, J=1.2, 8.1 Hz), 6.95 (6 H, brs), 6.98-7.04 (1 H, m), 7.69-7.72 (1 H, dd, J=1.8, 7.8 Hz).

EXAMPLE 9

Preparation of quinazolin-4-one

In a 2-mL volume stainless steel pressure-resistant vessel were placed 280 mg (1.8 mmol) of ammonium anthranilate (prepared in the same manner as in Reference Example 1), 400 mg (3.6 mmol) of methyl orthoformate, and 1.5 mL of methanol. The reaction was carried out at 120° C. for 2 hours. After the reaction was complete, the reaction mixture was cooled to room temperature and analyzed (according to absolute quantitative analysis) by high performance liquid chromatography. There was produced 214 mg (reaction yield: 81%) of quinazolin-4-one.

Reference Example 2

Preparation of ammonium 4-chloroanthranilate

In a 50 mL volume glass vessel equipped with a stirrer and a thermometer were placed 5.0 g (29.1 mmol) of 4-chloroanthranilic acid and 20 mL (156 mmol) of 15 wt. % ammonia methanol solution. The reaction was carried out for 2 hours at room temperature. After the reaction was complete, the reaction mixture was concentrated under reduced pressure, to obtain 5.0 g (isolated yield: 95%) of ammonium 4-chloroanthranilate as white solid.

The physical characteristics of the ammonium 4-chloroanthranilate (which was a new compound) were described below.

m.p. (sublimation): 232 to 233° C.

$^1$H-NMR (DMSO-$d_6$, δ (ppm)): 6.43 (1 H, dd, J=2.4, 8.4 Hz), 6.69 (1 H, d, J=2.4 Hz), 7.0 (3 H, brs), 7.69 (1 H, d, J=8.4 Hz), 11.0 (3 H, brs).

EXAMPLE 10

Preparation of 7-chloroquinazolin-4-one

In a 2-mL volume stainless steel pressure-resistant vessel were placed 340 mg (1.8 mmol) of ammonium 4-chloroanthranilate (prepared in the same manner as in Reference Example 2), 400 mg (3.6 mmol) of methyl orthoformate, and 1.5 mL of methanol. The reaction was carried out at 120° C. for 2 hours. After the reaction was complete, the reaction mixture was cooled to room temperature and analyzed (according to absolute quantitative analysis) by high performance liquid chromatography. There was produced 176 mg (reaction yield: 54%) of 7-chloroquinazolin-4-one.

Reference Example 3

Preparation of ammonium 5-chloroanthranilate

In a 50 mL volume glass vessel equipped with a stirrer and a thermometer were placed 5.0 g (29.1 mmol) of 5-chloroanthranilic acid and 20 mL (156 mmol) of 15 wt. % ammonia methanol solution. The reaction was carried out for 2 hours at room temperature. After the reaction was complete, the reaction mixture was concentrated under reduced pressure, to obtain 5.0 g (isolated yield: 95%) of ammonium 5-chloroanthranilate as pale yellow solid.

The physical characteristics of the ammonium 5-chloroanthranilate (which was a new compound) were described below.

m.p. (sublimation): 161 to 162° C.

$^1$H-NMR (DMSO-$d_6$, δ (ppm)): 6.57 (1 H, d, J=8.4 Hz), 6.99 (1 H, dd, J=2.7, 8.4 Hz), 7.0 (3 H, brs), 7.65 (1 H, d, J=2.7 Hz), 11.0 (3 H, brs).

EXAMPLE 11

Preparation of 6-chloroquinazolin-4-one

In a 2-mL volume stainless steel pressure-resistant vessel were placed 340 mg (1.8 mmol) of ammonium 5-chloroanthranilate (prepared in the same manner as in Reference Example 3), 400 mg (3.6 mmol) of methyl orthoformate, and 1.5 mL of methanol. The reaction was carried out at 120° C. for 2 hours. After the reaction was complete, the reaction mixture was cooled to room temperature and analyzed (according to absolute quantitative analysis) by high performance liquid chromatography. There was produced 307 mg (reaction yield: 94%) of 6-chloroquinazolin-4-one.

EXAMPLE 12

Preparation of 6-chloroquinazolin-4-one

In a 2-mL volume stainless steel pressure-resistant vessel were placed 340 mg (1.8 mmol) of ammonium 5-chloroanthranilate (prepared in the same manner as in Reference Example 3), 400 mg (3.6 mmol) of methyl orthoformate, and 1.5 mL of acetonitrile. The reaction was carried out at 120° C. for 2 hours. After the reaction was complete, the reaction mixture was cooled to room temperature and analyzed (according to absolute quantitative analysis) by high performance liquid chromatography. There was produced 303 mg (reaction yield: 93%) of 6-chloroquinazolin-4-one.

Reference Example 4

Preparation of ammonium 5-iodoanthranilate

In a 200 mL volume glass vessel equipped with a stirrer and a thermometer were placed 10.0 g (38 mmol) of 5-iodoanthranilic acid and 100 mL (780 mmol) of 15 wt. % ammonia methanol solution. The reaction was carried out for 3 hours at room temperature. After the reaction was complete, the reaction mixture was concentrated under reduced pressure, to obtain 9.0 g (isolated yield: 85%) of ammonium 5-iodoanthranilate as pale red solid.

The physical characteristics of the ammonium 5-iodoanthranilate (which was a new compound) were described below.

m.p. (decomposition): 160° C.

1H-NMR (DMSO-$d_6$, δ (ppm)): 6.45 (1 H, d, J=8.7 Hz), 6.5 (3 H, brs), 7.25 (1 H, dd, J=2.4, 8.7 Hz), 7.96 (1 H, d, J=2.4 Hz), 11.0 (3 H, brs).

EXAMPLE 13

Preparation of 6-iodoquinazolin-4-one

In a 2-mL volume stainless steel pressure-resistant vessel were placed 530 mg (1.9 mmol) of ammonium 5-iodoanthranilate (prepared in the same manner as in Reference Example 4), 403 mg (3.8 mmol) of methyl orthoformate, and 1.5 mL of methanol. The reaction was carried out at 120° C. for 2 hours. After the reaction was complete, the reaction mixture was cooled to room temperature and analyzed (according to absolute quantitative analysis) by high performance liquid chromatography. There was produced 402 mg (reaction yield: 77%) of 6-iodoquinazolin-4-one.

EXAMPLE 14

Preparation of 6-iodoquinazolin-4-one

In a 2-mL volume glass vessel equipped with a reflux condenser were placed 530 mg (1.9 mmol) of ammonium 5-iodoanthranilate (prepared in the same manner as in Reference Example 4), 403 mg (3.8 mmol) of methyl orthoformate, and 1.5 mL of n-butyl alcohol. The reaction was carried out at 120° C. for 2 hours. After the reaction was complete, the reaction mixture was cooled to room temperature and analyzed (according to absolute quantitative analysis) by high performance liquid chromatography. There was produced 350 mg (reaction yield: 67%) of 6-iodoquinazolin-4-one.

Utiliziation in Industry

According to the invention, quinazolin-4-one or its derivative can be prepared from anthranilic acid or its derivatives or ammonium anthranilate or its derivative in a high yield under moderate conditions by simple procedures.

What is claimed is:

1. A process for preparing quinazolin-4-one or a derivative thereof having the formula (2):

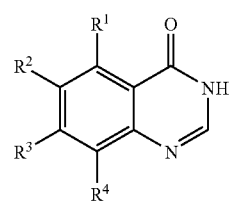

(2)

in which each of $R^1$, $R^2$, $R^3$ and $R^4$ independently represents a hydrogen atom, a halogen atom, or a group selected from the group consisting of alkyl, cycloalkyl, aralkyl, aryl, hydroxyl, alkoxy, alkylthio, nitro, and cyano, wherein a compound having the formula (1):

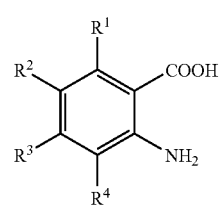

(1)

in which each of $R^1$, $R^2$, $R^3$ and $R^4$ has the same meaning as above, is reacted with a formic acid ester or an orthoformic acid ester at a temperature in the range of 50 to 150° C. in the presence of ammonia.

2. The process for preparing quinazolin-4-one or a derivative thereof according to claim 1, wherein each of $R^1$, $R^2$, $R^3$ and $R^4$ independently is a hydrogen atom or a halogen atom.

3. A process for preparing quinazolin-4-one or a derivative thereof having the formula (2):

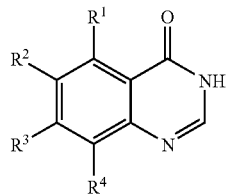

(2)

in which each of $R^1$, $R^2$, $R^3$ and $R^4$ independently represents a hydrogen atom, a halogen atom, or a group selected from the group consisting of alkyl, cycloalkyl, aralkyl, aryl, hydroxyl, alkoxy, alkylthio, nitro, and cyano, a compound having the formula (3):

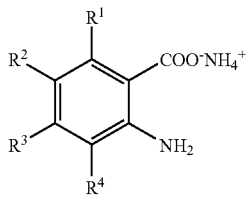

(3)

in which each of $R^1$, $R^2$, $R^3$ and $R^4$ has the same meaning as above, is reacted with a formic acid ester or an orthoformic acid ester at a temperature in the range of 50 to 150° C.

4. The process for preparing quinazolin-4-one or a derivative thereof according to claim 3, wherein each of $R^1$, $R^2$, $R^3$ and $R^4$ independently is a hydrogen atom or a halogen atom.

* * * * *